(12) United States Patent
Kusibojoska et al.

(10) Patent No.: US 6,911,024 B2
(45) Date of Patent: Jun. 28, 2005

(54) ABSORBENT ARTICLE

(75) Inventors: Liljana Kusibojoska, Gothenburg (SE); Kent Hermansson, Citrusgatan (SE)

(73) Assignee: SCA Hygiene Products AB, Gothenburg (SE)

( * ) Notice: Subject to any disclaimer, the term of this patent is extended or adjusted under 35 U.S.C. 154(b) by 272 days.

(21) Appl. No.: 10/151,040

(22) Filed: May 21, 2002

(65) Prior Publication Data

US 2002/0173766 A1 Nov. 21, 2002

Related U.S. Application Data

(60) Provisional application No. 60/291,945, filed on May 21, 2001.

(30) Foreign Application Priority Data

May 21, 2001 (SE) .............................................. 0101822

(51) Int. Cl.$^7$ ................................................ A61F 13/15
(52) U.S. Cl. ...................................... 604/392; 604/386
(58) Field of Search ........................... 604/386, 392–394

(56) References Cited

U.S. PATENT DOCUMENTS

| | | | |
|---|---|---|---|
| 5,135,522 A | | 8/1992 | Fahrenkrug et al. |
| 5,549,593 A | * | 8/1996 | Ygge et al. ................... 604/391 |
| 5,685,873 A | * | 11/1997 | Bruemmer ............. 604/385.24 |
| 5,695,849 A | | 12/1997 | Shawver et al. |

FOREIGN PATENT DOCUMENTS

| | | |
|---|---|---|
| EP | 0 287 388 A2 | 10/1988 |
| EP | 0 528 282 A2 | 2/1993 |
| EP | 0 528 282 A3 | 2/1993 |
| EP | 0 409 307 B1 | 9/1996 |
| EP | 0 605 012 B1 | 3/1999 |
| FR | 2 586 558 | 3/1987 |
| WO | 99/21522 | 5/1999 |

* cited by examiner

Primary Examiner—Larry I. Schwartz
Assistant Examiner—C. Lynne Anderson
(74) Attorney, Agent, or Firm—Young & Thompson

(57) ABSTRACT

Absorbent article includes a liquid pervious topsheet, a liquid impervious backsheet and an absorbent body enclosed therebetween. The article seen in longitudinal direction exhibits a front portion, a rear portion and a crotch portion therebetween, and a pair of belt portions attached to the rear portion alternatively the front portion and which are intended by the first fastening elements to be fastened together around the waist of the wearer and wherein the front portion alternatively rear portion exhibits second fastening elements intended to be attached to the belt portions, in such a way that the article will assume a pantlike shape, where the belt portions form a part of the waist portions of the pant. The belt portions exhibit a plurality of stiffening elements arranged on the inside of the belt portions at a certain distance from each other, in such a way that air gaps are formed between the skin of the wearer and the inside of the belt between the stiffening elements and the largest extension of the stiffening elements is arranged essentially across the belt in relation to the longitudinal direction of the belt.

12 Claims, 2 Drawing Sheets

ABSORBENT ARTICLE

TECHNICAL FIELD

The present invention relates to an absorbent article such as a diaper and incontinence guard comprising a liquid pervious topsheet, a liquid impervious backsheet and an absorbent body enclosed therebetween, whereby the article seen in longitudinal direction exhibits a front portion, a rear portion and a crotch portion therebetween, and further is provided with a pair of belt portions attached to the rear portion alternatively the front portion of the article and which are intended to be fastened together around the waist of the wearer by means of first fastening means and where said front portion alternatively the rear portion is provided with second fastening means intended to be attached to the belt portions, in such a way that the article will assume a pantlike shape, where the belt portions form a part of the waist portions of the pant.

BACKGROUND OF THE INVENTION

Diapers and incontinence guards for incontinent adults usually have a garment portion holding an absorbent body in place against the user's body and attachment means, which hold the garment portion in place also when the user is moving. A common type of attachment means are adhesive tapes or hook and loop fasteners of the touch-and close type which directly attach the front and rear portions of the absorbent article to each other. It is further known, through e.g., EP-A-0 287 388, EP-A-0 409 307, EP-A-0 528 282, EP-A-0 605 012 and FR-A-2 586 558, to attach the front and rear portions of the article by means of a belts at which the possibilities to adjust the fit are improved. The belt further provides a simplified change of diaper or incontinence guard, especially when the patient is standing up.

On a common type of belt diaper the belt portions are first attached around the waist of the patient and then the front portion of the diaper is attached to the outside of the belt using fastening means being arranged on the front portion, whereby the outsides of the belt serves as a reception surface for said fastening means.

Traditional belt materials have a tendency to fold themselves longitudinally upon usage and lie too close against the body. This is usually due to fact that the material does not exhibit the proper stiffness to be able to resist the different movements of the body and the pressure against the belt. The stiffness is usually improved by using a thicker material or a material being strongly bonded. Using this approach, the breathability of the material is considerably deteriorated and the belt feels warm and tight against the skin.

SUMMARY OF THE INVENTION

The object of the present invention is to provide a belt to a diaper or an incontinence guard being provided with a belt allowing an improved breathability. This object has been solved in that said belt portions exhibit a plurality of stiffening elements, being arranged on the inside of the belt portions on a certain distance from each other, in such a way that air gaps are being formed between the skin of the wearer and the inside of the belt between said stiffening elements, and the largest extension of said stiffening elements is arranged essentially across the belt in relation to the longitudinal direction of the belt. A possibility is thereby created for a change of air between the skin and the belt. In addition, the stiffening elements contribute to an improved stability and stiffness in the transversal direction of the belt, According to another aspect of the invention, the stiffening elements exhibit an outer wall of a steam and air permeable material having the capability to transport steam and an inner core comprising a material having a higher steam and air permeability than the outer wall of the stiffening elements. This design makes it possible to transport moisture and steam away from the skin being under the belt and lead to that the diaper feels more comfortable to wear, Further characteristics of the invention are evident from the following description and the dependent claims.

BRIEF DESCRIPTION OF DRAWINGS

The invention will in the following be closer described with reference to an embodiment shown in the accompanying drawings.

DETAILED DESCRIPTION OF THE INVENTION

Figure 1:
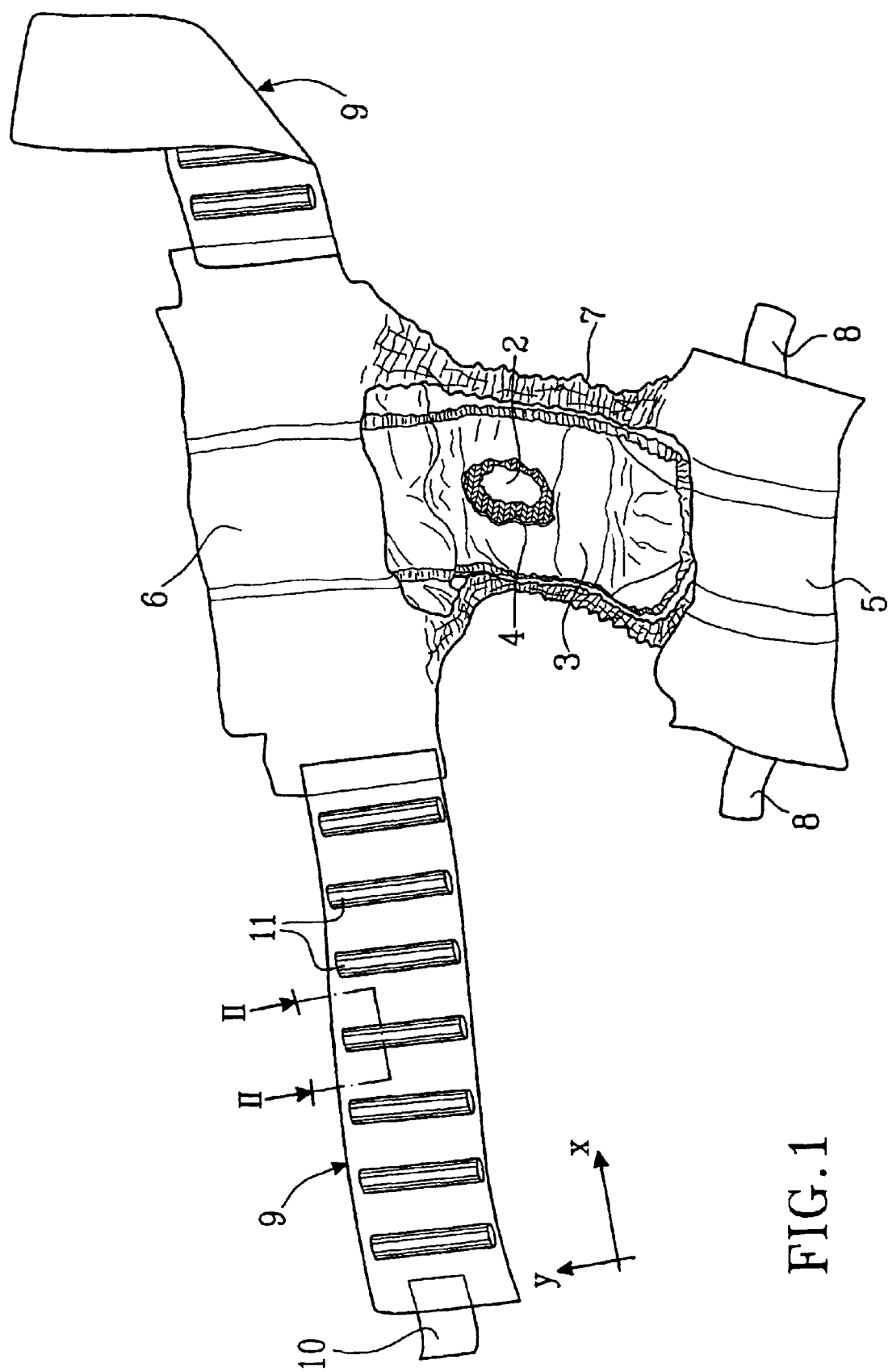
FIG. 1 shows schematically a perspective view from above of a diaper or incontinence guard according to the invention.
Figure 2:
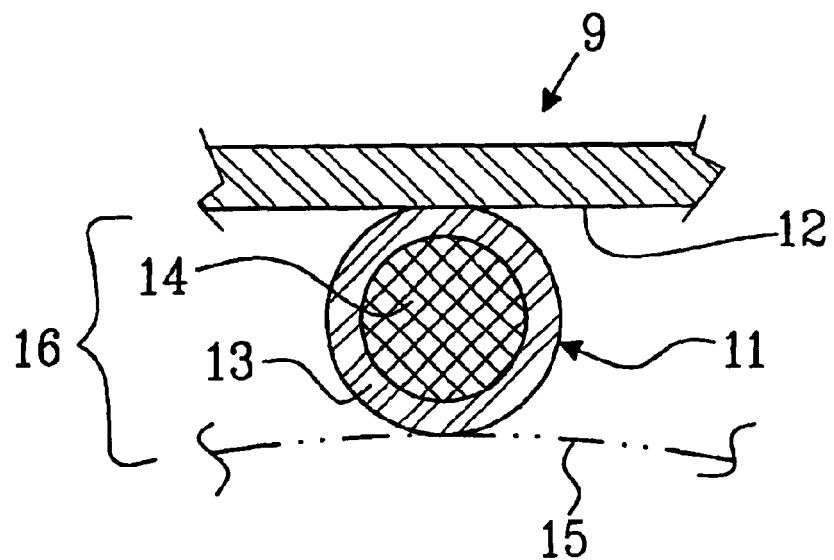
FIG. 2 shows a top view of a belt according to the invention.

FIG. 1 shows an embodiment of a diaper or incontinence guard 1 comprising a liquid impermeable backsheet 2, a liquid permeable topsheet 3 and an absorbent body 4 enclosed therebetween, The liquid permeable topsheet 3 can consist of a nonwoven material, e.g., a spunbond material of continuous filaments, a meltblown material, a bonded carded fibrous web or a perforated plastic film. The liquid impermeable backsheet 2 may consist of a plastic film, a nonwoven material coated with a liquid impervious material or a hydrophobic nonwoven material, which resists liquid penetration.

The backsheet material 2 and the topsheet 3 have a somewhat greater extension in the plane than the absorbent body 4 and extend outside the edges thereof. The layers 2 and 3 are connected to each other within the projecting portions thereof, e.g., by gluing or welding using heat or ultrasonic.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well known to a person skilled in the art and does therefore not have to be described in detail. The thin absorbent bodies, which are common in for example baby diapers and incontinence guards often, comprise a compressed mixed or layered structure of cellulosic fluff pulp and superabsorbent.

The diaper/incontinence guard is intended to enclose the lower part of the wearer's trunk like a pair of absorbent pants. It exhibits a front portion 5 intended during use to be worn on the front part of the user's body, a rear portion 6 intended during use to be worn on the rear part of the user's body, and a crotch portion 7 located between the front and rear portions and which is intended to be worn in the crotch part of the user between the legs.

A pair of belt portions 9 is with one end attached, e.g., glued or ultrasonically welded, to the rear portion 6 of the diaper. The belt portions 9 are with their opposite ends intended to be fastened together, by means of first fastening means 10, which for example can be hooks and loop type of fasteners or adhesive tape tabs. The outside portions of the belt portions 9 are reception surfaces for the fastening means 10. The fastening means 8 of the front portion 5 are intended to be attached against the outside portions of the belt portions 9 in order to fasten together the diaper/incontinence guard to the desired pantlike shape. The fastening means 8 can be hooks and loop type of fasteners or adhesive tape tabs. According to an alternative embodiment, the belt portions 9 are attached to the front portion 5 of the diaper and thus are intended to be fastened together on the back of the wearer, The fastening means 8 are then arranged on the rear portion 6 of the diaper.

The width of the belt portions 9 should be between 5–20 cm, preferably between 7–15 cm. The belt portions 9 are preferably a laminate of a carrier material, which forms the outside of the belt, and a soft nonwoven, which forms the inside of the belt intended to be in direct contact with the skin of the user. A suitable nonwoven material can be a spunbond material of e.g., polypropylene- or polyethylene fibres. Conjugate fibres may also be used. Another suitable nonwoven material can be a carded thermobonded material of e.g., polypropylene, polyester or conjugate fibres. A nonwoven or another suitable material can be used as carrier material. The carrier material should be adapted to function as a reception surface for the fastening means 8 and 10. Also elastic laminates are suitable to use as material in the belt portions 9.

According to the invention, the belt portions 9 are provided with a plurality of stiffening elements 11, being arranged essentially across the longitudinal direction x of the belt. The wording "across" used here, means that they extend between the opposite longitudinal edges of the belt portions 9, either essentially perpendicular to these edges or obliquely in relation to these edges. However, they do not have to extend all the way to the longitudinal edges of the belt portions 9, but may stop slightly inside these edges. The stiffening elements 11 ate arranged on the inside of the belt portions 12, i.e., the side being faced against the wearer. An air gap 16 is thereby being formed between the skin of the user 15 and the inside of the belt 12 between the stiffening elements 11, leading to an increased change of air between the belt portions 9 and the skin 15. This leads to that the belt feels more comfortable for the user to wear since the belt in this way "breathes".

According to a preferred embodiment of the invention the stiffening element 11 exhibits an outer wall and an inner core 14. The outer wall 13 of the stiffening element 11 comprises a steam and air permeable material and the inner core 14 comprises a material having a higher steam and air permeability than the outer wall 13 of the stiffening elements 11. Thereby a draught through said stiffening element 11 is achieved by a chimney effect making air and steam being transported away from the skin, up through the stiffening elements 11 and away from the belt.

Preferably, the material of the outer wall 13 of the stiffening elements 11 have a MVTR (Moisture Vapour Transmission Rate) value being at least about 2000 g/m$^3$/24 h or higher and the material of the inner core 14 a MVTR value exceeding the value for the outer wall 13 of the stiffening elements 11, leading to that a transport of moisture takes place. The measuring method for the estimation of MVTR is suitably ASTM E398, a method well known for a person skilled in the art.

The material of the outer wall 13 of the stiffening elements 11 is suitably a nonwoven material or a breathable plastic film, The inner core 14 preferably comprises an open foam material but may also consist of air. In the case of an air channel, a relatively high strength for the outer wall 13 of the stiffening element is required, in order to avoid that the channel collapses.

Upon usage of the stiffening elements 11 of the present invention, a belted article is achieved exhibiting a breathable belt, even if the material of the belt portions in itself is of a non-breathable material. The material in the belt portions can thus be freely chosen with respect to suitable properties such as strength, stiffness and density and still due to the stiffening elements 11 provide a breathable belt. It is also possible to chose a material, breathable or non-breathable, being well suited from a fastening point of view for the fastening means 10, but being too soft to alone function as a belt material, and which due to the stiffening elements 11 renders a higher stiffness. The stiffening elements 11 according to the invention are arranged on the inside 12 of the belt portions as being shown in FIG. 1, but the stiffening elements 11 could also be arranged inside the belt portions 9, for example as a part of a laminate. The important thing is that the chimney-like shape and function of the stiffening elements 11 is maintained and that an air gap is formed between the skin 15 and the inside 12 of the belt portions.

Figure 3:
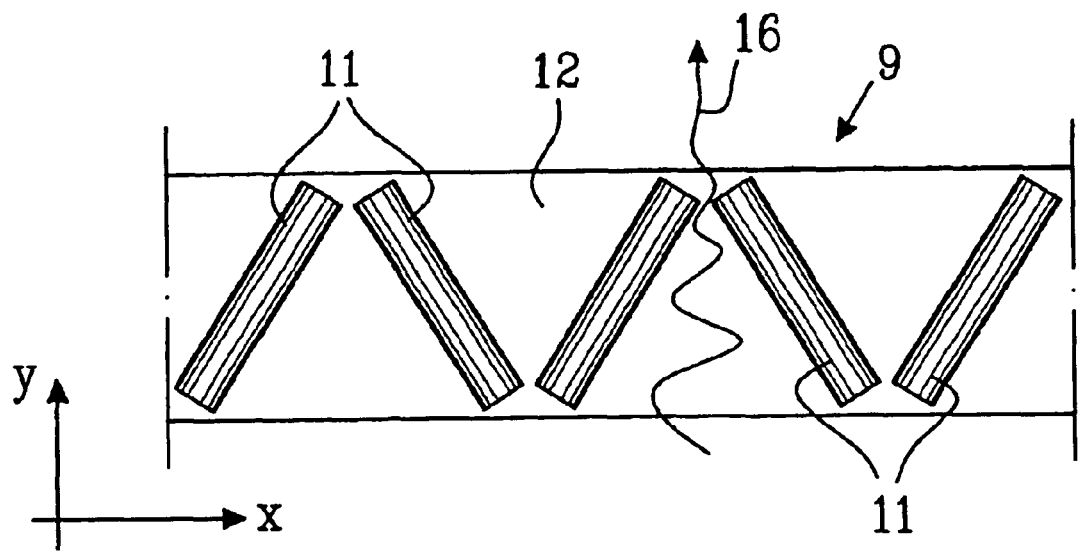
FIG. 3 shows an alternative placement of the stiffening element according to the invention.

The distance between the stiffening elements 11 should preferably be between 1 and 7 cm. It is preferred that said stiffening element 11 are arranged across the longitudinal direction x as straight tube shaped element (see FIG. 1), but said stiffening elements 11 can also be arranged in another pattern, for example in a zigzag pattern along the belt (see FIG. 3), as long as the function of the stiffening elements is maintained. Also, the stiffening elements 11 can be arranged on some parts of the belt portions 9.

The invention is of coarse not limited to the above described and on the drawings shown embodiment, but can be modified within the scope of the claims.

What is claimed is:

1. Absorbent article such as a diaper and incontinence guard comprising a liquid pervious topsheet, a liquid impervious backsheet and an absorbent body enclosed therebetween, whereby the article seen in longitudinal direction exhibits a front portion, a rear portion and a crotch portion therebetween, and further is provided with a pair of belt portions attached to the rear portion alternatively the front portion of the article and which are intended by means of first fastening means to be fastened together around the waist of a wearer and wherein said front portion alternatively rear portion exhibit second fastening means intended to be attached to the belt portions, in such a way that the article will assume a pantlike shape, where the belt portions form a part of the waist portions of the pant, wherein said belt portions exhibit a plurality of stiffening elements arranged on the inside of the belt portions at a certain distance from each other, in such a way that air gaps are formed between the skin of the wearer and the inside of the belt between said stiffening elements and the largest extension of said stiffening elements is arranged essentially across the belt in relation to the longitudinal direction of the belt, each stiffening element having a cross-sectional thickness which is substantially greater than the cross-sectional thickness of each belt portion.

2. Absorbent article according to claim 1, wherein said stiffening elements are arranged in a striped pattern or a crosswise pattern.

3. Absorbent article according to claim 1, wherein said stiffening elements are arranged at a mutual distance between 1 cm and 7 cm.

4. Absorbent article such as a diaper and incontinence guard comprising a liquid pervious topsheet, a liquid impervious backsheet and an absorbent body enclosed therebetween, whereby the article seen in longitudinal direction exhibits a front portion, a rear portion and a crotch portion therebetween, and further is provided with a pair of belt portions attached to the rear portion alternatively the front portion of the article and which are intended by means of first fastening means to be fastened together around the waist of a wearer and wherein said front portion alternatively rear portion exhibit second fastening means intended to be attached to the belt portions, in such a way that the article will assume a pantlike shape, where the belt portions form a part of the waist portions of the pant, wherein said belt portions exhibit a plurality of stiffening elements arranged on the inside of the belt portions at a certain distance from each other, in such a way that air gaps are formed between the skin of the wearer and the inside of the belt between said stiffening elements and the largest extension of said stiffening elements is arranged essentially across the belt in relation to the longitudinal direction of the belt, said stiffening elements comprising an outer wall of a steam and air permeable material having the capability to transport steam, and an inner core comprising a material having a higher steam and air permeability than the outer wall.

5. Absorbent article according to claim 4, wherein the outer wall of the stiffening element exhibits a MVTR (Moisture Vapour Transmission Rate) value being at least about 2000 g/m$^3$/24 h and that the inner core of the stiffening elements exhibits a MVTR value exceeding the MVTR value for the outer wall of the stiffening elements.

6. Absorbent article according to claim 4, wherein said stiffening elements are arranged in a striped pattern or a crosswise pattern.

7. Absorbent article according to claim 4, wherein said stiffening elements are arranged at a mutual distance between 1 cm and 7 cm.

8. Absorbent article such as a diaper and incontinence guard comprising a liquid pervious topsheet, a liquid impervious backsheet and an absorbent body enclosed therebetween, whereby the article seen in longitudinal direction exhibits a front portion, a rear portion and a crotch portion therebetween, and further is provided with a pair of belt portions attached to the rear portion alternatively the front portion of the article and which are intended by means of first fastening means to be fastened together around the waist of a wearer and wherein said front portion alternatively rear portion exhibit second fastening means intended to be attached to the belt portions, in such a way that the article will assume a pantlike shape, where the belt portions form a part of the waist portions of the pant, wherein said belt portions exhibit a plurality of stiffening elements arranged on the inside of the belt portions at a certain distance from each other, in such a way that air gaps are formed between the skin of the wearer and the inside of the belt between said stiffening elements and the largest extension of said stiffening elements is arranged essentially across the belt in relation to the longitudinal direction of the belt, each of said stiffening elements comprising a tubular-shaped member.

9. Absorbent article according to claim 8, wherein said stiffening elements are arranged in a striped pattern or a crosswise pattern.

10. Absorbent article according to claim 8, wherein said stiffening elements are arranged at a mutual distance between 1 cm and 7 cm.

11. Absorbent article according to claim 8, wherein said stiffening elements comprise an outer wall of a steam and air permeable material having the capability to transport steam and an inner core comprising a material having a higher steam and air permeability than the outer wall of the stiffening elements.

12. Absorbent article according to claim 11, wherein the outer wall of the stiffening element exhibits a MVTR (Moisture Vapour Transmission Rate) value being at least about 2000 g/m$^3$/24 h and that the inner core of the stiffening elements exhibits a MVTR value exceeding the MVTR value for the outer wall of the stiffening elements.

* * * * *